US007105325B2

(12) United States Patent
Yu et al.

(10) Patent No.: US 7,105,325 B2
(45) Date of Patent: *Sep. 12, 2006

(54) HUMAN HYDROXYLASES AND POLYNUCLEOTIDES ENCODING THE SAME

(75) Inventors: Xuanchuan Yu, Conroe, TX (US); Maricar Miranda, Houston, TX (US); Yi Hu, Spring, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/029,636

(22) Filed: Jan. 5, 2005

(65) Prior Publication Data

US 2005/0176042 A1    Aug. 11, 2005

Related U.S. Application Data

(63) Continuation of application No. 10/154,674, filed on May 23, 2002, now Pat. No. 6,867,025.

(60) Provisional application No. 60/294,076, filed on May 29, 2001.

(51) Int. Cl.
*C12N 9/02* (2006.01)
*C12N 15/53* (2006.01)

(52) U.S. Cl. ................. 435/184; 435/320.1; 435/252.3

(58) Field of Classification Search ..................... None
See application file for complete search history.

(56) References Cited

U.S. PATENT DOCUMENTS

| | | | |
|---|---|---|---|
| 4,215,051 A | 7/1980 | Schroeder et al. | |
| 4,376,110 A | 3/1983 | David et al. | |
| 4,594,595 A | 6/1986 | Struckman | |
| 4,631,211 A | 12/1986 | Houghten | |
| 4,689,405 A | 8/1987 | Frank et al. | |
| 4,713,326 A | 12/1987 | Dattagupta et al. | |
| 4,873,191 A | 10/1989 | Wagner et al. | |
| 4,946,778 A | 8/1990 | Ladner et al. | |
| 5,252,743 A | 10/1993 | Barrett et al. | |
| 5,272,057 A | 12/1993 | Smulson et al. | |
| 5,424,186 A | 6/1995 | Fodor et al. | |
| 5,445,934 A | 8/1995 | Fodor et al. | |
| 5,459,127 A | 10/1995 | Felgner et al. | |
| 5,556,752 A | 9/1996 | Lockhart et al. | |
| 5,700,637 A | 12/1997 | Southern | |
| 5,723,323 A | 3/1998 | Kauffman et al. | |
| 5,744,305 A | 4/1998 | Fodor et al. | |
| 5,830,721 A | 11/1998 | Stemmer et al. | |
| 5,837,458 A | 11/1998 | Minshull et al. | |
| 5,869,336 A | 2/1999 | Meyer et al. | |
| 5,877,397 A | 3/1999 | Lonberg et al. | |
| 5,948,767 A | 9/1999 | Scheule et al. | |
| 6,048,850 A | 4/2000 | Young et al. | |
| 6,075,181 A | 6/2000 | Kucherlapati et al. | |
| 6,110,490 A | 8/2000 | Thierry | |
| 6,114,598 A | 9/2000 | Kucherlapati et al. | |
| 6,150,584 A | 11/2000 | Kucherlapati et al. | |

OTHER PUBLICATIONS

Bird et al, 1988, "Single-Chain Antigen-Binding Proteins", Science 242:423-426.
Bitter et al, 1987, "Expression and Secretion Vectors for Yeast", Methods in Enzymology 153:516-544.
Colbere-Garapin et al, 1981, "A New Dominant Hybrid Selective Marker for Higher Eukaryotic Cells", J. Mol. Biol. 150:1-14.
Cote et al, 1983, "Generation of human monoclonal antibodies reactive with cellular.antigens", PNAS 80:2026-2030.
Gautier et al, 1987, "α-DNA IV:α-anomeric and β-anomeric tetrahymidylates covalently linked to intercalating oxazolopyridocarbazole. Synthesis, physiochemical properties and poly (rA) binding", Nucleic Acids Research 15(16):6625-6641.
Gordon, 1989, "Transgenic Animals", International Review of Cytology, 115:171-229.
Greenspan et al, 1993, "Idiotypes: structure and immunogenicity", FASEB Journal 7:437-444.
Gu et al, 1994, "Deletion of a DNA Polymerase β Gene Segment in T Cells Using Cell Type-Specific Gene Targeting", Science 265:103-106.
Huse et al, 1989, "Generation of a Large Combinatorial Library of the Immunoglobulin Repertoire in Phage Lambda", Science 246:1275-1281.
Huston et al, 1988, "Protein engineering of antibody binding sites: Recovery of specific activity in an anti-digoxin single-chain Fv analogue produced in *Escherichia coli*", Proc. Natl. Acad. Sci. USA 85:5879-5883.
Inoue et al, 1987, "Sequence-dependent hydrolysis of RNA using modified oligonucleotide splints and R Nase H", FEBS Letters 215(2):327-330.
Inoue et al, 1987, "Synthesis and hybridization studies on two complementary nona(2'-O-methyl)ribonucleotides", Nucleic Acids Research 15(15):6131-6149.
Inouye & Inouye, 1985, "Up-promoter mutations in the Ipp gene of *Escherichia coli*", Nucleic Acids Research 13(9):3101-3110.
Janknecht et al, 1991, "Rapid and efficient purification of native histidine-tagged protein expressed by recombinant vaccinia virus", PNAS 88:8972-8976.
Kohler & Milstein, 1975, "Continuous cultures of fused cells secreting antibody of predefined specificity", Nature 256:495-497.
Lakso et al, 1992, "Targeted oncogene activation by site-specific recombination in transgenic mice", Proc. Natl. Acad. Sci. USA 89:6232-6236.
Lavitrano et al, 1989, "Sperm Cells as Vectors for Introducing Foreign DNA into Eggs: Genetic Transformation of Mice", Cell 57:717-723.
Lo, 1983, "Transformation by Iontophoretic Microinjection of DNA: Multiple Integrations without Tandem Insertions", Mol. & Cell. Biology 3(10):1803-1814.
Logan et al, 1984, "Adenovirus tripartite leader sequence enhances of mRNAs late after infection", Proc. Natl. Acad. Sci. USA 81:3655-3659.

(Continued)

*Primary Examiner*—Charles L. Patterson, Jr.

(57) ABSTRACT

Noval human polynucleotide and polypeptide sequences are disclosed that can be used in industrial, therapeutic, diagnostic, and pharmacogenomic applications.

20 Claims, No Drawings

OTHER PUBLICATIONS

Lowy et al, 1980, "Isolation of Transforming DNA: Cloning the Hamster aprt Gene", Cell 22:817-823.

Morrison et al, 1984, "Chimeric human antibody molecules: Mouse antigen-binding domains with human constant region domains", Proc. Natl. Acad. Sci. USA 81:6851-6855.

Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.

Ruther et al, 1983, "Easy identification of cDNA clones", EMBO Journal 2(10):1791-1794.

Santerre et al, 1984, "Expression of prokaryotic genes for hygromycin B and G418 rersistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the Autographa californica Nuclear Polyhedrosis Virus Genome: Deletion Mutations within the Polyhedrin Gene", J. Virol. 46(2):584-593.

Stein et al, 1988, "Physiochemical properties of phosphorothioate oligodeoxynucleotides", Nucleic Acids Research 16(8):3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026-2034.

Takeda et al, 1985, "Construction of chimaeric processed immunoglobulin containing mouse variable and human constant region sequences", Nature 314:452-454.

Thompson et al, 1989, "Germ Line Transmission and Expression of a Corrected HPRT Gene Produced by Gene Targeting in Embryonic Stem Cells", Cell 56:313-321.

Van Der Putten et al, 1985, "Efficient insertion of genes into the mouse germ line via retroviral vectors", Proc. Natl. Acad. Sci. USA 82:6148-6152.

Van Heeke et al, 1989, "Expression of Human Asparagine Synthetase in *Escherichia coli*", J. Biol. Chemistry 264(10):5503-5509.

Ward et al, 1989, "Binding activities of a repertoire of single Immunoglobulin variable domains secreted from *Escherichia coli*", Nature 341:544-546.

Wigler et al, 1980, "Transformation of mammalian cells with an amplifiable dominant-acting gene", Proc. Natl. Acad. Sci. USA 77(6):3567-3570.

Green, C.D., et al., Tryptophan Hydroxylase Expression Is Regulated By a Circadian Clock in Xenopus laevis Retina. J. Neuro. 1994, vol. 62, pp. 2420-2428.

Grenett, H.E., et al., Full-Length cDNA For Rabbit Tryptophan Hydroxylase: Functional Domains and Evolution Of Aromatic Amino Acid Hydroxylases. Proc. Natl. Acad. Sci., USA. Aug. 1987, vol. 84, pp. 5530-5534.

Robson, K.J.H. et al., Polysome Immunopreciapitation Of Phenylalanine Hydroxylase mRNA From Rat Liver and Cloning of Its cDNA. Proc. Natl. Acad. Sci., USA. Aug. 1982, vol. 79, pp. 4701-4705.

Grima, B., et al., Complete Coding Sequence of Rat Tyrosine Hydroxylase mRNA. Proc. Natl. Acad. Sci., USA., Jan. 1985, vol. 82, pp. 617-621.

International Search Report, PCT/US02/16635 (2004).

__US 7,105,325 B2__

SEQUENCE LISTING

```
<160> NUMBER OF SEQ ID NOS: 8

<210> SEQ ID NO 1
<211> LENGTH: 1473
<212> TYPE: DNA
<213> ORGANISM: homo sapiens

<400> SEQUENCE: 1
atgcagccag caatgatgat gttttccagt aaatactggg cacggagagg gttttccctg      60
gattcagcag tgcccgaaga gcatcagcta cttggcagct caacactaaa taaacctaac     120
tctggcaaaa atgacgacaa aggcaacaag ggaagcagca aacgtgaagc tgctaccgaa     180
agtggcaaga cagcagttgt tttctccttg aagaatgaag ttggtggatt ggtaaaagca     240
ctgaggctct ttcaggaaaa acgtgtcaac atggttcata ttgaatccag gaaatctcgg     300
cgaagaagtt ctgaggttga aatctttgtg gactgtgagt gtgggaaaac agaattcaat     360
gagctcattc agttgctgaa atttcaaacc actattgtga cgctgaatcc tccagagaac     420
atttggacag aggaagaaga gctagaggat gtgccctggt tccctcggaa gatctctgag     480
ttagacaaat gctctcacag agttctcatg tatggttctg agcttgatgc tgaccaccca     540
ggatttaagg acaatgtcta tcgacagaga agaaagtatt ttgtggatgt ggccatgggt     600
tataaatatg gtcagcccat tcccagggtg gagtatactg aagaagaaac taaaacttgg     660
```

```
ggtgttgtat tccgggagct ctccaaactc tatcccactc atgcttgccg agagtatttg    720
aaaaacttcc ctctgctgac taaatactgt ggctacagag aggacaatgt gcctcaactc    780
gaagatgtct ccatgtttct gaaagaaagg tctggcttca cggtgaggcc ggtggctgga    840
tacctgagcc cacgagactt tctggcagga ctggcctaca gagtgttcca ctgtacccag    900
tacatccggc atggctcaga tcccctctac accccagaac cagacacatg ccatgaactc    960
ttgggacatg ttccactact tgcggatcct aagtttgctc agttttcaca gaaataggt    1020 ctggcgtctc tggagcatc agatgaagat gttcagaaac tagccacgtg ctatttcttc    1080
acaatcgagt ttggcctttg caagcaagaa gggcaactgc gggcatatgg agcaggactc    1140
ctttcctcca ttggagaatt aaagcacgcc ctttctgaca aggcatgtgt gaaagccttt    1200
gacccaaaga caacttgctt acaggaatgc cttatcacca ccttccagga agcctacttt    1260
gtttcagaaa gttttgaaga agccaaagaa aagatgaggg actttgcaaa gtcaattacc    1320
cgtcccttct cagtatactt caatccctac acacagagta ttgaaattct gaaagacacc    1380
agaagtattg aaaatgtggt gcaggacctt cgcagcgact gaatacagt gtgtgatgct    1440 ttaaacaaaa tgaaccaata tctggggatt tga                                1473
```

<210> SEQ ID NO 2
<211> LENGTH: 490
<212> TYPE: PRT
<213> ORGANISM: homo sapiens

<400> SEQUENCE: 2

```
Met Gln Pro Ala Met Met Met Phe Ser Ser Lys Tyr Trp Ala Arg Arg
 1               5                  10                  15

Gly Phe Ser Leu Asp Ser Ala Val Pro Glu Glu His Gln Leu Leu Gly
                20                  25                  30

Ser Ser Thr Leu Asn Lys Pro Asn Ser Gly Lys Asn Asp Asp Lys Gly
            35                  40                  45

Asn Lys Gly Ser Ser Lys Arg Glu Ala Ala Thr Glu Ser Gly Lys Thr
        50                  55                  60

Ala Val Val Phe Ser Leu Lys Asn Glu Val Gly Gly Leu Val Lys Ala
65                  70                  75                  80

Leu Arg Leu Phe Gln Glu Lys Arg Val Asn Met Val His Ile Glu Ser
                85                  90                  95

Arg Lys Ser Arg Arg Arg Ser Ser Glu Val Glu Ile Phe Val Asp Cys
            100                 105                 110

Glu Cys Gly Lys Thr Glu Phe Asn Glu Leu Ile Gln Leu Leu Lys Phe
        115                 120                 125

Gln Thr Thr Ile Val Thr Leu Asn Pro Pro Glu Asn Ile Trp Thr Glu
    130                 135                 140

Glu Glu Glu Leu Glu Asp Val Pro Trp Phe Pro Arg Lys Ile Ser Glu
145                 150                 155                 160

Leu Asp Lys Cys Ser His Arg Val Leu Met Tyr Gly Ser Glu Leu Asp
                165                 170                 175

Ala Asp His Pro Gly Phe Lys Asp Asn Val Tyr Arg Gln Arg Arg Lys
            180                 185                 190

Tyr Phe Val Asp Val Ala Met Gly Tyr Lys Tyr Gly Gln Pro Ile Pro
        195                 200                 205

Arg Val Glu Tyr Thr Glu Glu Glu Thr Lys Thr Trp Gly Val Val Phe
    210                 215                 220
```

-continued

Arg Glu Leu Ser Lys Leu Tyr Pro Thr His Ala Cys Arg Glu Tyr Leu
225                 230                 235                 240

Lys Asn Phe Pro Leu Leu Thr Lys Tyr Cys Gly Tyr Arg Glu Asp Asn
                245                 250                 255

Val Pro Gln Leu Glu Asp Val Ser Met Phe Leu Lys Glu Arg Ser Gly
            260                 265                 270

Phe Thr Val Arg Pro Val Ala Gly Tyr Leu Ser Pro Arg Asp Phe Leu
        275                 280                 285

Ala Gly Leu Ala Tyr Arg Val Phe His Cys Thr Gln Tyr Ile Arg His
    290                 295                 300

Gly Ser Asp Pro Leu Tyr Thr Pro Glu Pro Asp Thr Cys His Glu Leu
305                 310                 315                 320

Leu Gly His Val Pro Leu Leu Ala Asp Pro Lys Phe Ala Gln Phe Ser
                325                 330                 335

Gln Glu Ile Gly Leu Ala Ser Leu Gly Ala Ser Asp Glu Asp Val Gln
            340                 345                 350

Lys Leu Ala Thr Cys Tyr Phe Phe Thr Ile Glu Phe Gly Leu Cys Lys
        355                 360                 365

Gln Glu Gly Gln Leu Arg Ala Tyr Gly Ala Gly Leu Leu Ser Ser Ile
    370                 375                 380

Gly Glu Leu Lys His Ala Leu Ser Asp Lys Ala Cys Val Lys Ala Phe
385                 390                 395                 400

Asp Pro Lys Thr Thr Cys Leu Gln Glu Cys Leu Ile Thr Thr Phe Gln
                405                 410                 415

Glu Ala Tyr Phe Val Ser Glu Ser Phe Glu Glu Ala Lys Glu Lys Met
            420                 425                 430

Arg Asp Phe Ala Lys Ser Ile Thr Arg Pro Phe Ser Val Tyr Phe Asn
        435                 440                 445

Pro Tyr Thr Gln Ser Ile Glu Ile Leu Lys Asp Thr Arg Ser Ile Glu
    450                 455                 460

Asn Val Val Gln Asp Leu Arg Ser Asp Leu Asn Thr Val Cys Asp Ala
465                 470                 475                 480

Leu Asn Lys Met Asn Gln Tyr Leu Gly Ile
                485                 490

<210> SEQ ID NO 3
<211> LENGTH: 1461
<212> TYPE: DNA
<213> ORGANISM: homo sapiens

<400> SEQUENCE: 3

```
atgatgatgt tttccagtaa atactgggca cggagagggt tttccctgga ttcagcagtg    60
cccgaagagc atcagctact tggcagctca acactaaata aacctaactc tggcaaaaat   120
gacgacaaag gcaacaaggg aagcagcaaa cgtgaagctg ctaccgaaag tggcaagaca   180
gcagttgttt tctccttgaa gaatgaagtt ggtggattgg taaaagcact gaggctcttt   240
caggaaaaac gtgtcaacat ggttcatatt gaatccagga atctcggcg aagaagttct   300 gaggttgaaa tctttgtgga ctgtgagtgt gggaaaacag aattcaatga gctcattcag   360
ttgctgaaat tcaaaccac tattgtgacg ctgaatcctc cagagaacat ttggacagag   420
gaagaagagc tagaggatgt gccctggttc cctcggaaga tctctgagtt agacaaatgc   480
tctcacagag ttctcatgta tggttctgag cttgatgctg accacccagg atttaaggac   540
aatgtctatc gacagagaag aaagtatttt gtggatgtgg ccatgggtta taaatatggt   600
```

-continued

```
cagcccattc ccagggtgga gtatactgaa gaagaaacta aaacttgggg tgttgtattc      660
cgggagctct ccaaactcta tcccactcat gcttgccgag agtatttgaa aaacttccct      720
ctgctgacta atactgtgg ctacagagag acaatgtgc ctcaactcga agatgtctcc       780
atgtttctga agaaaggtc tggcttcacg gtgaggccgg tggctggata cctgagccca      840
cgagactttc tggcaggact ggcctacaga gtgttccact gtacccagta catccggcat      900
ggctcagatc ccctctacac cccagaacca gacacatgcc atgaactctt gggacatgtt     960
ccactacttg cggatcctaa gtttgctcag ttttcacaag aaataggtct ggcgtctctg     1020
ggagcatcag atgaagatgt tcagaaacta gccacgtgct atttcttcac aatcgagttt     1080
ggcctttgca agcaagaagg gcaactgcgg gcatatggag caggactcct ttcctccatt     1140
ggagaattaa agcacgccct ttctgacaag gcatgtgtga agcctttga cccaaagaca      1200 acttgcttac aggaatgcct tatcaccacc ttccaggaag cctactttgt ttcagaaagt     1260
tttgaagaag ccaaagaaaa gatgagggac tttgcaaagt caattacccg tcccttctca     1320
gtatacttca atccctacac acagagtatt gaaattctga agacaccag aagtattgaa      1380 aatgtggtgc aggaccttcg cagcgacttg aatacagtgt gtgatgcttt aaacaaaatg    1440
aaccaatatc tggggatttg a                                               1461
```

<210> SEQ ID NO 4
<211> LENGTH: 486
<212> TYPE: PRT
<213> ORGANISM: homo sapiens

<400> SEQUENCE: 4

```
Met Met Met Phe Ser Ser Lys Tyr Trp Ala Arg Arg Gly Phe Ser Leu
 1               5                   10                  15

Asp Ser Ala Val Pro Glu Glu His Gln Leu Leu Gly Ser Ser Thr Leu
            20                  25                  30

Asn Lys Pro Asn Ser Gly Lys Asn Asp Asp Lys Gly Asn Lys Gly Ser
        35                  40                  45

Ser Lys Arg Glu Ala Ala Thr Glu Ser Gly Lys Thr Ala Val Val Phe
    50                  55                  60

Ser Leu Lys Asn Glu Val Gly Gly Leu Val Lys Ala Leu Arg Leu Phe
65                  70                  75                  80

Gln Glu Lys Arg Val Asn Met Val His Ile Glu Ser Arg Lys Ser Arg
                85                  90                  95

Arg Arg Ser Ser Glu Val Glu Ile Phe Val Asp Cys Glu Cys Gly Lys
            100                 105                 110

Thr Glu Phe Asn Glu Leu Ile Gln Leu Leu Lys Phe Gln Thr Thr Ile
        115                 120                 125

Val Thr Leu Asn Pro Pro Glu Asn Ile Trp Thr Glu Glu Glu Leu
    130                 135                 140

Glu Asp Val Pro Trp Phe Pro Arg Lys Ile Ser Glu Leu Asp Lys Cys
145                 150                 155                 160

Ser His Arg Val Leu Met Tyr Gly Ser Glu Leu Asp Ala Asp His Pro
                165                 170                 175

Gly Phe Lys Asp Asn Val Tyr Arg Gln Arg Arg Lys Tyr Phe Val Asp
            180                 185                 190

Val Ala Met Gly Tyr Lys Tyr Gly Gln Pro Ile Pro Arg Val Glu Tyr
        195                 200                 205

Thr Glu Glu Glu Thr Lys Thr Trp Gly Val Val Phe Arg Glu Leu Ser
    210                 215                 220
```

```
Lys Leu Tyr Pro Thr His Ala Cys Arg Glu Tyr Leu Lys Asn Phe Pro
225                 230                 235                 240

Leu Leu Thr Lys Tyr Cys Gly Tyr Arg Glu Asp Asn Val Pro Gln Leu
            245                 250                 255

Glu Asp Val Ser Met Phe Leu Lys Glu Arg Ser Gly Phe Thr Val Arg
        260                 265                 270

Pro Val Ala Gly Tyr Leu Ser Pro Arg Asp Phe Leu Ala Gly Leu Ala
    275                 280                 285

Tyr Arg Val Phe His Cys Thr Gln Tyr Ile Arg His Gly Ser Asp Pro
290                 295                 300

Leu Tyr Thr Pro Glu Pro Asp Thr Cys His Glu Leu Leu Gly His Val
305                 310                 315                 320

Pro Leu Leu Ala Asp Pro Lys Phe Ala Gln Phe Ser Gln Glu Ile Gly
                325                 330                 335

Leu Ala Ser Leu Gly Ala Ser Asp Glu Asp Val Gln Lys Leu Ala Thr
            340                 345                 350

Cys Tyr Phe Phe Thr Ile Glu Phe Gly Leu Cys Lys Gln Glu Gly Gln
        355                 360                 365

Leu Arg Ala Tyr Gly Ala Gly Leu Leu Ser Ser Ile Gly Glu Leu Lys
    370                 375                 380

His Ala Leu Ser Asp Lys Ala Cys Val Lys Ala Phe Asp Pro Lys Thr
385                 390                 395                 400

Thr Cys Leu Gln Glu Cys Leu Ile Thr Thr Phe Gln Glu Ala Tyr Phe
                405                 410                 415

Val Ser Glu Ser Phe Glu Glu Ala Lys Glu Lys Met Arg Asp Phe Ala
            420                 425                 430

Lys Ser Ile Thr Arg Pro Phe Ser Val Tyr Phe Asn Pro Tyr Thr Gln
        435                 440                 445

Ser Ile Glu Ile Leu Lys Asp Thr Arg Ser Ile Glu Asn Val Val Gln
    450                 455                 460

Asp Leu Arg Ser Asp Leu Asn Thr Val Cys Asp Ala Leu Asn Lys Met
465                 470                 475                 480

Asn Gln Tyr Leu Gly Ile
                485

<210> SEQ ID NO 5
<211> LENGTH: 1458
<212> TYPE: DNA
<213> ORGANISM: homo sapiens

<400> SEQUENCE: 5
atgatgtttt ccagtaaata ctgggcacgg agagggtttt ccctggattc agcagtgccc      60
gaagagcatc agctacttgg cagctcaaca ctaaataaac ctaactctgg caaaaatgac     120
gacaaaggca acaagggaag cagcaaacgt gaagctgcta ccgaaagtgg caagacagca     180
gttgttttct ccttgaagaa tgaagttggt ggattggtaa aagcactgag gctctttcag     240
gaaaaacgtg tcaacatggt tcatattgaa tccaggaaat ctcggcgaag aagttctgag     300
gttgaaatct tgtggactg tgagtgtggg aaaacagaat tcaatgagct cattcagttg     360
ctgaaatttc aaaccactat tgtgacgctg aatcctccag agaacatttg acagaggaa     420 gaagagctag aggatgtgcc ctggttccct cggaagatct ctgagttaga caaatgctct     480
cacagagttc tcatgtatgg ttctgagctt gatgctgacc acccaggatt taaggacaat     540
gtctatcgac agagaagaaa gtattttgtg gatgtggcca tgggttataa atatggtcag     600
```

```
cccattccca gggtggagta tactgaagaa gaaactaaaa cttggggtgt tgtattccgg    660
gagctctcca aactctatcc cactcatgct tgccgagagt atttgaaaaa cttccctctg    720
ctgactaaat actgtggcta cagagaggac aatgtgcctc aactcgaaga tgtctccatg    780
tttctgaaag aaaggtctgg cttcacggtg aggccggtgg ctggatacct gagcccacga    840
gactttctgg caggactggc ctacagagtg ttccactgta cccagtacat ccggcatggc    900
tcagatcccc tctacacccc agaaccagac acatgccatg aactcttggg acatgttcca    960
ctacttgcgg atcctaagtt tgctcagttt tcacaagaaa taggtctggc gtctctggga   1020
gcatcagatg aagatgttca gaaactagcc acgtgctatt tcttcacaat cgagtttggc   1080
ctttgcaagc aagaagggca actgcgggca tatggagcag gactcctttc ctccattgga   1140
gaattaaagc acgccctttc tgacaaggca tgtgtgaaag cctttgaccc aaagacaact   1200
tgcttacagg aatgccttat caccaccttc caggaagcct actttgtttc agaaagtttt   1260
gaagaagcca agaaaagat gagggacttt gcaaagtcaa ttacccgtcc cttctcagta   1320
tacttcaatc cctacacaca gagtattgaa attctgaaag acaccagaag tattgaaaat   1380
gtggtgcagg accttcgcag cgacttgaat acagtgtgtg atgctttaaa caaaatgaac   1440
caatatctgg ggatttga                                                 1458
```

<210> SEQ ID NO 6
<211> LENGTH: 485
<212> TYPE: PRT
<213> ORGANISM: homo sapiens

<400> SEQUENCE: 6

```
Met Met Phe Ser Ser Lys Tyr Trp Ala Arg Arg Gly Phe Ser Leu Asp
 1               5                  10                  15

Ser Ala Val Pro Glu Glu His Gln Leu Leu Gly Ser Ser Thr Leu Asn
            20                  25                  30

Lys Pro Asn Ser Gly Lys Asn Asp Lys Gly Asn Lys Gly Ser Ser
        35                  40                  45

Lys Arg Glu Ala Ala Thr Glu Ser Gly Lys Thr Ala Val Val Phe Ser
    50                  55                  60

Leu Lys Asn Glu Val Gly Gly Leu Val Lys Ala Leu Arg Leu Phe Gln
65                  70                  75                  80

Glu Lys Arg Val Asn Met Val His Ile Glu Ser Arg Lys Ser Arg Arg
                85                  90                  95

Arg Ser Ser Glu Val Glu Ile Phe Val Asp Cys Glu Cys Gly Lys Thr
            100                 105                 110

Glu Phe Asn Glu Leu Ile Gln Leu Leu Lys Phe Gln Thr Thr Ile Val
        115                 120                 125

Thr Leu Asn Pro Pro Glu Asn Ile Trp Thr Glu Glu Glu Leu Glu
    130                 135                 140

Asp Val Pro Trp Phe Pro Arg Lys Ile Ser Glu Leu Asp Lys Cys Ser
145                 150                 155                 160

His Arg Val Leu Met Tyr Gly Ser Glu Leu Asp Ala Asp His Pro Gly
                165                 170                 175

Phe Lys Asp Asn Val Tyr Arg Gln Arg Arg Lys Tyr Phe Val Asp Val
            180                 185                 190

Ala Met Gly Tyr Lys Tyr Gly Gln Pro Ile Pro Arg Val Glu Tyr Thr
        195                 200                 205

Glu Glu Glu Thr Lys Thr Trp Gly Val Val Phe Arg Glu Leu Ser Lys
```

-continued

```
              210                 215                 220
Leu Tyr Pro Thr His Ala Cys Arg Glu Tyr Leu Lys Asn Phe Pro Leu
225                 230                 235                 240

Leu Thr Lys Tyr Cys Gly Tyr Arg Glu Asp Asn Val Pro Gln Leu Glu
                245                 250                 255

Asp Val Ser Met Phe Leu Lys Glu Arg Ser Gly Phe Thr Val Arg Pro
            260                 265                 270

Val Ala Gly Tyr Leu Ser Pro Arg Asp Phe Leu Ala Gly Leu Ala Tyr
        275                 280                 285

Arg Val Phe His Cys Thr Gln Tyr Ile Arg His Gly Ser Asp Pro Leu
    290                 295                 300

Tyr Thr Pro Glu Pro Asp Thr Cys His Glu Leu Leu Gly His Val Pro
305                 310                 315                 320

Leu Leu Ala Asp Pro Lys Phe Ala Gln Phe Ser Gln Glu Ile Gly Leu
                325                 330                 335

Ala Ser Leu Gly Ala Ser Asp Glu Asp Val Gln Lys Leu Ala Thr Cys
            340                 345                 350

Tyr Phe Phe Thr Ile Glu Phe Gly Leu Cys Lys Gln Glu Gly Gln Leu
        355                 360                 365

Arg Ala Tyr Gly Ala Gly Leu Leu Ser Ser Ile Gly Glu Leu Lys His
    370                 375                 380

Ala Leu Ser Asp Lys Ala Cys Val Lys Ala Phe Asp Pro Lys Thr Thr
385                 390                 395                 400

Cys Leu Gln Glu Cys Leu Ile Thr Thr Phe Gln Glu Ala Tyr Phe Val
                405                 410                 415

Ser Glu Ser Phe Glu Glu Ala Lys Glu Lys Met Arg Asp Phe Ala Lys
            420                 425                 430

Ser Ile Thr Arg Pro Phe Ser Val Tyr Phe Asn Pro Tyr Thr Gln Ser
        435                 440                 445

Ile Glu Ile Leu Lys Asp Thr Arg Ser Ile Glu Asn Val Val Gln Asp
    450                 455                 460

Leu Arg Ser Asp Leu Asn Thr Val Cys Asp Ala Leu Asn Lys Met Asn
465                 470                 475                 480

Gln Tyr Leu Gly Ile
                485
```

<210> SEQ ID NO 7
<211> LENGTH: 1455
<212> TYPE: DNA
<213> ORGANISM: homo sapiens

<400> SEQUENCE: 7

| | | | | | |
|---|---|---|---|---|---|
| atgttttcca | gtaaatactg | ggcacggaga | gggttttccc | tggattcagc | agtgcccgaa | 60 |
| gagcatcagc | tacttggcag | ctcaacacta | aataaaccta | actctggcaa | aaatgacgac | 120 |
| aaaggcaaca | agggaagcag | caaacgtgaa | gctgctaccg | aaagtggcaa | gacagcagtt | 180 |
| gttttctcct | tgaagaatga | agttggtgga | ttggtaaaag | cactgaggct | ctttcaggaa | 240 |
| aaacgtgtca | acatggttca | tattgaatcc | aggaaatctc | ggcgaagaag | ttctgaggtt | 300 |
| gaaatctttg | tggactgtga | gtgtgggaaa | acagaattca | tgagctcat | tcagttgctg | 360 |
| aaatttcaaa | ccactattgt | gacgctgaat | cctccagaga | catttggac | agaggaagaa | 420 |
| gagctagagg | atgtgccctg | gttccctcgg | aagatctctg | agttagacaa | atgctctcac | 480 |
| agagttctca | tgtatggttc | tgagcttgat | gctgaccacc | caggatttaa | ggacaatgtc | 540 |

-continued

```
tatcgacaga gaagaaagta ttttgtggat gtggccatgg gttataaata tggtcagccc    600
attcccaggg tggagtatac tgaagaagaa actaaaactt ggggtgttgt attccgggag    660
ctctccaaac tctatcccac tcatgcttgc cgagagtatt tgaaaaactt ccctctgctg    720
actaaatact gtggctacag agaggacaat gtgcctcaac tcgaagatgt ctccatgttt    780
ctgaaagaaa ggtctggctt cacggtgagg ccggtggctg gatacctgag cccacgagac    840
tttctggcag gactggccta cagagtgttc cactgtaccc agtacatccg gcatggctca    900
gatcccctct acaccccaga accagacaca tgccatgaac tcttgggaca tgttccacta    960
cttgcggatc ctaagtttgc tcagttttca caagaaatag gtctggcgtc tctgggagca   1020
tcagatgaag atgttcagaa actagccacg tgctatttct tcacaatcga gtttggcctt   1080
tgcaagcaag aagggcaact gcgggcatat ggagcaggac tcctttcctc cattggagaa   1140
ttaaagcacg ccctttctga caaggcatgt gtgaaagcct ttgacccaaa gacaacttgc   1200
ttacaggaat gccttatcac caccttccag gaagcctact tgtttcaga aagttttgaa    1260 gaagccaaag aaaagatgag ggactttgca agtcaatta cccgtccctt ctcagtatac    1320
ttcaatccct acacacagag tattgaaatt ctgaaagaca ccagaagtat tgaaaatgtg    1380
gtgcaggacc ttcgcagcga cttgaataca gtgtgtgatg cttttaaacaa aatgaaccaa   1440 tatctgggga tttga                                                     1455
```

<210> SEQ ID NO 8
<211> LENGTH: 484
<212> TYPE: PRT
<213> ORGANISM: homo sapiens

<400> SEQUENCE: 8

```
Met Phe Ser Ser Lys Tyr Trp Ala Arg Arg Gly Phe Ser Leu Asp Ser
  1               5                  10                  15

Ala Val Pro Glu Glu His Gln Leu Leu Gly Ser Ser Thr Leu Asn Lys
             20                  25                  30

Pro Asn Ser Gly Lys Asn Asp Asp Lys Gly Asn Lys Gly Ser Ser Lys
         35                  40                  45

Arg Glu Ala Ala Thr Glu Ser Gly Lys Thr Ala Val Phe Ser Leu
     50                  55                  60

Lys Asn Glu Val Gly Gly Leu Val Lys Ala Leu Arg Leu Phe Gln Glu
 65                  70                  75                  80

Lys Arg Val Asn Met Val His Ile Glu Ser Arg Lys Ser Arg Arg Arg
                 85                  90                  95

Ser Ser Glu Val Glu Ile Phe Val Asp Cys Glu Cys Gly Lys Thr Glu
            100                 105                 110

Phe Asn Glu Leu Ile Gln Leu Leu Lys Phe Gln Thr Thr Ile Val Thr
        115                 120                 125

Leu Asn Pro Pro Glu Asn Ile Trp Thr Glu Glu Glu Leu Glu Asp
    130                 135                 140

Val Pro Trp Phe Pro Arg Lys Ile Ser Glu Leu Asp Lys Cys Ser His
145                 150                 155                 160

Arg Val Leu Met Tyr Gly Ser Glu Leu Asp Ala Asp His Pro Gly Phe
                165                 170                 175

Lys Asp Asn Val Tyr Arg Gln Arg Arg Lys Tyr Phe Val Asp Val Ala
            180                 185                 190

Met Gly Tyr Lys Tyr Gly Gln Pro Ile Pro Arg Val Glu Tyr Thr Glu
        195                 200                 205
```

-continued

```
Glu Glu Thr Lys Thr Trp Gly Val Val Phe Arg Glu Leu Ser Lys Leu
    210                 215                 220

Tyr Pro Thr His Ala Cys Arg Glu Tyr Leu Lys Asn Phe Pro Leu Leu
225                 230                 235                 240

Thr Lys Tyr Cys Gly Tyr Arg Glu Asp Asn Val Pro Gln Leu Glu Asp
                245                 250                 255

Val Ser Met Phe Leu Lys Glu Arg Ser Gly Phe Thr Val Arg Pro Val
            260                 265                 270

Ala Gly Tyr Leu Ser Pro Arg Asp Phe Leu Ala Gly Leu Ala Tyr Arg
        275                 280                 285

Val Phe His Cys Thr Gln Tyr Ile Arg His Gly Ser Asp Pro Leu Tyr
    290                 295                 300

Thr Pro Glu Pro Asp Thr Cys His Glu Leu Leu Gly His Val Pro Leu
305                 310                 315                 320

Leu Ala Asp Pro Lys Phe Ala Gln Phe Ser Gln Glu Ile Gly Leu Ala
                325                 330                 335

Ser Leu Gly Ala Ser Asp Glu Asp Val Gln Lys Leu Ala Thr Cys Tyr
            340                 345                 350

Phe Phe Thr Ile Glu Phe Gly Leu Cys Lys Gln Glu Gly Gln Leu Arg
        355                 360                 365

Ala Tyr Gly Ala Gly Leu Leu Ser Ser Ile Gly Glu Leu Lys His Ala
370                 375                 380

Leu Ser Asp Lys Ala Cys Val Lys Ala Phe Asp Pro Lys Thr Thr Cys
385                 390                 395                 400

Leu Gln Glu Cys Leu Ile Thr Thr Phe Gln Glu Ala Tyr Phe Val Ser
                405                 410                 415

Glu Ser Phe Glu Glu Ala Lys Glu Lys Met Arg Asp Phe Ala Lys Ser
            420                 425                 430

Ile Thr Arg Pro Phe Ser Val Tyr Phe Asn Pro Tyr Thr Gln Ser Ile
        435                 440                 445

Glu Ile Leu Lys Asp Thr Arg Ser Ile Glu Asn Val Val Gln Asp Leu
    450                 455                 460

Arg Ser Asp Leu Asn Thr Val Cys Asp Ala Leu Asn Lys Met Asn Gln
465                 470                 475                 480

Tyr Leu Gly Ile
```

HUMAN HYDROXYLASES AND POLYNUCLEOTIDES ENCODING THE SAME

The present application is a continuation application of U.S. application Ser. No. 10/154,674, filed on May 23, 2002, which issued as U.S. Pat. No. 6,867,025 on Mar. 15, 2005, which claims the benefit of U.S. Provisional Application No. 60/294,076, which was filed on May 29, 2001, each of which are herein incorporated by reference in their entirety.

1. INTRODUCTION

The present invention relates to the discovery, identification, and characterization of novel human polynucleotides encoding proteins sharing sequence similarity with mammalian hydroxylases. The invention encompasses the described polynucleotides, host cell expression systems, the encoded protein, fusion proteins, polypeptides and peptides, antibodies to the encoded proteins and peptides, and genetically engineered animals that either lack or overexpress the disclosed polynucleotides, antagonists and agonists of the proteins, and other compounds that modulate the expression or activity of the proteins encoded by the disclosed polynucleotides, which can be used for diagnosis, drug screening, clinical trial monitoring, the treatment of diseases and disorders, and cosmetic or nutriceutical applications.

2. BACKGROUND OF THE INVENTION

Hydroxylases are enzymes that mediate the cleavage of hydroxyl groups, and many hydroxylases act in biological pathways suitable for drug intervention.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal hydroxylases, and particularly tryptophan hydroxylases, which are involved in a rate-limiting step in the biosynthesis of a number of neurologically active compounds, including, but not limited to, DOPA, serotonin and melatonin. Given the well known physiological functions of the above compounds, the described hydroxylases can be used to identify and/or develop agents useful for modulating behavior (i.e., treating anxiety, depression, hyperactivity, sleep disorders, etc.). The novel human nucleic acid (cDNA) sequences described herein encode proteins/open reading frames (ORFs) of 490, 486, 485, and 484 amino acids in length (SEQ ID NOS:2, 4, 6, and 8, respectively).

In addition to the direct therapeutic use of the described NHPs, the invention also encompasses agonists and antagonists of the described NHPS, including small molecules, large molecules, mutant NHPS; or portions thereof, that compete with native NHPS, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knockout mice can be produced in several ways, one of which involves the use of mouse embryonic stem cell ("ES cell") lines that contain gene trap mutations in a murine homolog of at least one of the described NHPS. When the unique NHP sequences described in SEQ ID NOS:1–8 are "knocked-out" they provide a method of identifying phenotypic expression of the particular gene, as well as a method of assigning function to previously unknown genes. In addition, animals in which the unique NHP sequences described in SEQ ID NOS:1–8 are "knocked-out" provide a unique source in which to elicit antibodies to homologous and orthologous proteins, which would have been previously viewed by the immune system as "self" and therefore would have failed to elicit significant antibody responses.

Additionally, the unique NHP sequences described in SEQ ID NOS:1–8 are useful for the identification of protein coding sequences, and mapping a unique gene to a particular chromosome. These sequences identify biologically verified exon splice junctions, as opposed to splice junctions that may have been bioinformatically predicted from genomic sequence alone. The sequences of the present invention are also useful as additional DNA markers for restriction fragment length polymorphism (RFLP) analysis, and in forensic biology, particularly given the presence of a nucleotide polymorphism within the described sequences.

Further, the present invention also relates to processes for identifying compounds that modulate, i.e., act as agonists or antagonists of, NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the ORFs encoding the described NHP amino acid sequences.

5. DETAILED DESCRIPTION OF THE INVENTION

The NHPs described for the first time herein are novel proteins that can be expressed in, inter alia, human cell lines, human fetal brain, spinal cord, lymph node, prostate, testis, thyroid, pancreas, pericardium, hypothalamus, fetal kidney, fetal lung, 6 and 9-week old embryos, osteosarcoma, and embryonic carcinoma cells.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of a NHP that correspond to functional domains of a NHP, and the polypeptide products specified by such nucleotide sequences, including, but not limited to, the novel regions of any active domain(s); (c) isolated nucleotides that encode mutant versions, engineered or naturally occurring, of a described NHP, in which all or a part of at least one domain is deleted or altered, and the polypeptide products specified by such nucleotide sequences, including, but not limited to, soluble proteins and peptides; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides, such as oligonucleotides, antisense polynucleotides, ribozymes, dsRNA, or gene therapy constructs, comprising a sequence first disclosed in the Sequence Listing.

As discussed above, the present invention includes the human DNA sequences presented in the Sequence Listing (and vectors comprising the same), and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., New York, at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species, and mutant NHPs, whether naturally occurring or engineered (by site directed mutagenesis, gene shuffling, directed evolution as described in, for example, U.S. Pat. Nos. 5,837,458 and 5,723,323 both of which are herein incorporated by reference in their entirety). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package, as described herein, using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a microarray or high-throughput "chip" format). Additionally, a series of NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–8 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–8, or an amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445, 934, 5,252,743, 4,713,326, 5,424,186, and 4,689,405, the disclosures of which are herein incorporated by reference in their entirety.

Addressable arrays comprising sequences first disclosed in SEQ ID NOS:1–8 can be used to identify and characterize the temporal and tissue specific expression of a gene. These addressable arrays incorporate oligonucleotide sequences of sufficient length to confer the required specificity, yet be within the limitations of the production technology. The length of these probes is usually within a range of between about 8 to about 2000 nucleotides. Preferably the probes consist of 60 nucleotides, and more preferably 25 nucleotides, from the sequences first disclosed in SEQ ID NOS: 1–8.

For example, a series of such NHP oligonucleotide sequences, or the complements thereof, can be used in chip format to represent all or a portion of the described sequences. The oligonucleotides, typically between about 16 to about 40 (or any whole number within the stated range) nucleotides in length, can partially overlap each other, and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing, and proceed in either a sense (5'-to-3') orientation vis-a-vis the described sequence or in an antisense orientation.

Microarray-based analysis allows the discovery of broad patterns of genetic activity, providing new understanding of gene functions, and generating novel and unexpected insight into transcriptional processes and biological mechanisms. The use of addressable arrays comprising sequences first disclosed in SEQ ID NOS:1–8 provides detailed information about transcriptional changes involved in a specific pathway, potentially leading to the identification of novel components, or gene functions that manifest themselves as novel phenotypes.

Probes consisting of sequences first disclosed in SEQ ID NOS:1–8 can also be used in the identification, selection, and validation of novel molecular targets for drug discovery. The use of these unique sequences permits the direct confirmation of drug targets, and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1–8 can be utilized in microarrays, or other assay formats, to screen collections of genetic material from patients who have a particular medical condition. These investigations can also be carried out using the sequences first disclosed in SEQ ID NOS:1–8 in silico, and by comparing previously collected genetic databases and the disclosed sequences using computer software known to those in the art.

Thus the sequences first disclosed in SEQ ID NOS:1–8 can be used to identify mutations associated with a particular disease, and also in diagnostic or prognostic assays.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence, in conjunction with the presence of one or more specific oligonucleotide sequence(s) first disclosed in SEQ ID NOS: 1–8. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP antisense molecules, useful, for example, in NHP gene regulation and/or as antisense primers in amplification reactions of NHP nucleic acid sequences. With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Spring Harbor Press, Cold Spring Harbor, N.Y. (and periodic updates thereof), and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be genomic DNA, or total RNA, mRNA, and/or cDNA obtained by reverse transcription of mRNA prepared from human or non-human cell lines or tissue known to express, or suspected of expressing, an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a NHP gene, such as, for example, testis tissue) A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see, e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known to express, or suspected of expressing, a NHP, in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of carrying, or known to carry, a mutant NHP allele (e.g., a person manifesting a NHP-associated phenotype such as, for example, neurological disorders, such as, but not limited to, depression, anxiety, Alzheimer's disease or Parkinson's disease, obesity, high blood pressure, connective tissue disorders, infertility, developmental disorders, etc.), or a cDNA library can be constructed using RNA from a tissue known to express, or suspected of expressing, a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known to express, or suspected of expressing, a mutant NHP allele in an individual suspected of carrying, or known to carry, such a mutant allele. In this manner, gene products made by the putatively mutant tissue can be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to a NHP are likely to cross-react with a corresponding mutant NHP expression product. Library clones detected via their reaction with such labeled antibodies can be purified and subjected to sequence analysis according to methods well-known in the art.

The invention also encompasses: (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators, and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 or adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPS, or inappropriately expressed NHPS, for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to a NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway), can be used to directly treat diseases or disorders. For instance, the administration of an effective amount of a soluble NHP (or, for example, a suitably derivatized NHP, e.g., with polyethylene glycol (PEG), albumin, etc.), a NHP-IgFc fusion protein, or an anti-idiotypic antibody (or its Fab) that mimics the NHP, could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules, can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The described sequences were compiled from human gene trapped sequences, and cDNAs made from human fetal brain, fetal lung, and lymph node mRNAs (Edge Biosystems, Gaithersburg, Md.). As biologically validated (spliced and polyadenylated sequences), the described sequences are useful for mapping the corresponding coding region of the human genome and particularly for mapping exon splice junctions. The described NHPs are apparently encoded on human chromosome 12 (see GEN-BANK accession no. AC023966).

An A/T polymorphism was detected during the sequencing of the NHPs at the nucleotide position represented by, for example, position 1125 of SEQ ID NO:1 (and the corresponding location in the other NHP nucleotide sequences), both of which result in an ala at the region corresponding to amino acid (aa) position 375 of, for example, SEQ ID NO:2 (and the corresponding location in the other NHP amino acid sequences). As these polymorphisms are coding single nucleotide polymorphisms (SNPs), they are particularly useful in forensic analysis.

An additional application of the described novel human polynucleotide sequences is their use in the molecular mutagenesis/evolution of proteins that are at least partially encoded by the described novel sequences using, for example, polynucleotide shuffling or related methodologies.

Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees, may be used to generate NHP transgenic animals.

Any technique known in the art may be used to introduce a NHP transgene into animals to produce the founder lines of transgenic animals. Such techniques include, but are not limited to, pronuclear microinjection (Hoppe and Wagner, 1989, U.S. Pat. No. 4,873,191); retrovirus-mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry a NHP transgene in all their cells, as well as animals that carry a transgene in some, but not all their cells, i.e., mosaic animals or somatic cell transgenic animals. A transgene may be integrated as a single transgene, or in concatamers, e.g., head-to-head tandems or head-to-tail tandems. A transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of NHP gene-expressing tissue may also be evaluated immunocytochemically using antibodies specific for the NHP transgene product.

The present invention also provides for "knock-in" animals. Knock-in animals are those in which a polynucleotide sequence (i.e., a gene or a cDNA) that the animal does not naturally have in its genome is inserted in such a way that it is expressed. Examples include, but are not limited to, a human gene or cDNA used to replace its murine ortholog in the mouse, a murine cDNA used to replace the murine gene in the mouse, and a human gene or cDNA or murine cDNA that is tagged with a reporter construct used to replace the murine ortholog or gene in the mouse. Such replacements can occur at the locus of the murine ortholog or gene, or at another specific site. Such knock-in animals are useful for the in vivo study, testing and validation of, intra alia, human drug targets, as well as for compounds that are directed at the same, and therapeutic proteins.

5.2 NHPS and NHP Polypeptides

NHPs, NHP polypeptides, NHP peptide fragments, mutated, truncated, or deleted forms of the NHPS, and/or NHP fusion proteins can be prepared for a variety of uses. These uses include, but are not limited to, the generation of antibodies, as therapeutic products (particularly in the treatment of behavioral disorders such as, but not limited to, dementia, insomnia, depression, anorexia, and premenstrual syndrome, etc., as well as cancers such as, but not limited to, lymphoma, leukemia, sarcomas, carcinomas, myelomas, etc.), as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.) in order to treat disease, or to therapeutically augment the efficacy of therapeutic or chemotherapeutic agents. In addition, the described NHPs can be used in drug screening assays similar to those described in, for example, U.S. Pat. No. 6,048,850, herein incorporated by reference, in order to identify compounds for treating diseases such as, for example, depression, anxiety, immune disorders, Alzheimer's disease, epilepsy, and Parkinson's disease.

The Sequence Listing discloses the amino acid sequences encoded by the described NHP polynucleotides. The NHPs display initiator methionines in DNA sequence contexts consistent with translation initiation sites, and a N-terminal signal sequence characteristic of secreted or membrane proteins (the signal sequence is often cleaved from the mature form of the protein incident to the protein translocating across the membrane).

The NHP amino acid sequences of the invention include the amino acid sequences presented in the Sequence Listing, as well as analogues and derivatives thereof, as well as any oligopeptide sequence of at least about 10–40 amino acids, about 12–35 amino acids, or about 16–30 amino acids in length first disclosed in the Sequence Listing. Further, corresponding NHP homologues from other species are encompassed by the invention. In fact, any NHP encoded by the NHP nucleotide sequences described herein are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to the NHPs encoded by the presently described nucleotide sequences, as judged by any of a number of criteria, including, but not limited to, the ability to bind and cleave a substrate of a NHP, the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described herein, but that result in a silent change, thus producing a functionally equivalent expression product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP products or NHP polypeptides can be produced in soluble or secreted forms (by removing one or more transmembrane domains where applicable), the peptide or polypeptide can be recovered from the culture media. Such expression systems also encompass engineered host cells that express a NHP, or a functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of a NHP, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing a NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in-frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target expression product can be released from the GST moiety.

In an exemplary insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into a non-essential region (for example the polyhedrin gene) of the virus and placed under control of an AcNPV promoter (for example the polyhedrin promoter). Successful insertion of a NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J., Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., see Logan and Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the desired modification and processing of the foreign protein expressed. To this end, eukaryotic host cells that possess the cellular machinery for the desired processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express a NHP product. Such engineered cell lines may be particularly useful in screening and evaluation of compounds that affect the endogenous activity of a NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. Another exemplary system allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto Ni$^{2+}$•nitriloacetic acid-agarose columns, and histidine-tagged proteins are selectively eluted with imidazole-containing buffers.

Also encompassed by the present invention are fusion proteins that direct a NHP to a target organ and/or facilitate transport across the membrane into the cytosol. Conjugation of NHPs to antibody molecules or their Fab fragments could be used to target cells bearing a particular epitope. Attaching an appropriate signal sequence to a NHP would also transport a NHP to a desired location within the cell. Alternatively targeting of a NHP or its nucleic acid sequence might be achieved using liposome or lipid complex based delivery systems. Such technologies are described in "Liposomes: A Practical Approach", New, R. R. C., ed., Oxford University Press, N.Y., and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of NHPs to a target site or desired organ, where they cross the cell membrane and/or the nucleus where the NHPs can exert their functional activity. This goal may be achieved by coupling of a NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences), to facilitate passage across cellular membranes, and can optionally be engineered to include nuclear localization signals.

Additionally contemplated are oligopeptides that are modeled on an amino acid sequence first described in the Sequence Listing. Such NHP oligopeptides are generally between about 10 to about 100 amino acids long, or between about 16 to about 80 amino acids long, or between about 20 to about 35 amino acids long, or any variation or combination of sizes represented therein that incorporate a contiguous region of sequence first disclosed in the Sequence Listing. Such NHP oligopeptides can be of any length disclosed within the above ranges and can initiate at any amino acid position represented in the Sequence Listing.

The invention also contemplates "substantially isolated" or "substantially pure" proteins or polypeptides. By a "substantially isolated" or "substantially pure" protein or polypeptide is meant a protein or polypeptide that has been separated from at least some of those components that naturally accompany it. Typically, the protein or polypeptide is substantially isolated or pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially isolated or pure protein or polypeptide may be obtained, for example, by extraction from a natural source, by expression of a recombinant nucleic acid encoding the protein or polypeptide, or by chemically synthesizing the protein or polypeptide.

Purity can be measured by any appropriate method, e.g., column chromatography such as immunoaffinity chromatography using an antibody specific for the protein or polypeptide, polyacrylamide gel electrophoresis, or HPLC analysis. A protein or polypeptide is substantially free of naturally associated components when it is separated from at least some of those contaminants that accompany it in its natural state. Thus, a polypeptide that is chemically synthesized or produced in a cellular system different from the cell from which it naturally originates will be, by definition, substantially free from its naturally associated components. Accordingly, substantially isolated or pure proteins or polypeptides include eukaryotic proteins synthesized in *E. coli*, other prokaryotes, or any other organism in which they do not naturally occur.

5.3 Antibodies to NHP Products

Antibodies that specifically recognize one or more epitopes of a NHP, epitopes of conserved variants of a NHP, or peptide fragments of a NHP, are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of a NHP in a biological sample and may, therefore, be utilized as part of a diagnostic or prognostic technique whereby patients may be tested for abnormal amounts of a NHP. Such antibodies may also be utilized in conjunction with, for example, compound screening schemes for the evaluation of the effect of test compounds on expression and/or activity of a NHP expression product. Additionally, such antibodies can be used in conjunction with gene therapy to, for example, evaluate normal and/or engineered NHP-expressing cells prior to their introduction into a patient. Such antibodies may additionally be used in methods for the inhibition of abnormal NHP activity. Thus, such antibodies may be utilized as a part of treatment methods.

For the production of antibodies, various host animals may be immunized by injection with a NHP, a NHP peptide (e.g., one corresponding to a functional domain of a NHP), a truncated NHP polypeptide (a NHP in which one or more domains have been deleted), functional equivalents of a NHP, or mutated variants of a NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and/or, coupling with molecules such as keyhole limpet hemocyanin, tetanus toxoid, diphtheria toxoid, ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, and IgD, and any subclass thereof. The hybridomas producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of an antibody molecule; and Fab fragments, which can be generated by reducing the disulfide bridges of F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nissinoff, 1991, J. Immunol. 147:2429–2438). For example, antibodies that bind to a NHP domain and competitively inhibit the binding of a NHP to its cognate receptor can be used to generate anti-idiotypes that "mimic" the NHP and, therefore, bind and activate or neutralize a receptor. Such anti-idiotypic antibodies, or Fab fragments of such anti-idiotypes, can be used in therapeutic regimens involving a NHP-mediated pathway.

Additionally given the high degree of relatedness of mammalian NHPs, NHP knock-out mice (having never seen a NHP, and thus never been tolerized to a NHP) have a unique utility, as they can be advantageously applied to the generation of antibodies against the disclosed mammalian NHPs (i.e., a NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising an isolated nucleic acid molecule that encodes the amino acid sequence shown in SEQ ID NO:8.

2. The recombinant expression vector of claim 1, wherein said isolated nucleic acid molecule comprises the nucleic acid sequence of SEQ ID NO:7.

3. The recombinant expression vector of claim 1, wherein said isolated nucleic acid molecule encodes the amino acid sequence shown in SEQ ID NO:6.

4. The recombinant expression vector of claim 3, wherein said isolated nucleic acid molecule comprises the nucleic acid sequence of SEQ ID NO:5.

5. The recombinant expression vector of claim 3, wherein said isolated nucleic acid molecule encodes the amino acid sequence shown in SEQ ID NO:4.

6. The recombinant expression vector of claim 5, wherein said isolated nucleic acid molecule comprises the nucleic acid sequence of SEQ ID NO:3.

7. The recombinant expression vector of claim 5, wherein said isolated nucleic acid molecule encodes the amino acid sequence shown in SEQ ID NO:2.

8. The recombinant expression vector of claim 7, wherein said isolated nucleic acid molecule comprises the nucleic acid sequence of SEQ ID NO:1.

9. A host cell comprising the recombinant expression vector of claim 1.

10. The host cell of claim 9, wherein said recombinant expression vector comprises the nucleic acid sequence of SEQ ID NO:7.

11. The host cell of claim 9, wherein said recombinant expression vector encodes the amino acid sequence shown in SEQ ID NO:6.

12. The host cell of claim 11, wherein said recombinant expression vector comprises the nucleic acid sequence of SEQ ID NO:5.

13. The host cell of claim 11, wherein said recombinant expression vector encodes the amino acid sequence shown in SEQ ID NO:4.

14. The host cell of claim 13, wherein said recombinant expression vector comprises the nucleic acid sequence of SEQ ID NO:3.

15. The host cell of claim 13, wherein said recombinant expression vector encodes the amino acid sequence shown in SEQ ID NO:2.

16. The host cell of claim 15, wherein said recombinant expression vector comprises the nucleic acid sequence of SEQ ID NO:1.

17. An isolated polypeptide comprising the amino acid sequence of SEQ ID NO:8.

18. The isolated polypeptide of claim 17, wherein said polypeptide comprises the amino acid sequence of SEQ ID NO:6.

19. The isolated polypeptide of claim 18, wherein said polypeptide comprises the amino acid sequence of SEQ ID NO:4.

20. The isolated polypeptide of claim 19, wherein said polypeptide comprises the amino acid sequence of SEQ ID NO:2.

* * * * *